United States Patent [19]

Tsunoda et al.

[11] 4,322,564

[45] Mar. 30, 1982

[54] PROCESS FOR HYDROFORMYLATION OF OLEFINS

[75] Inventors: Yoshitoshi Tsunoda; Shimpei Tomita; Chihiro Miyazawa, all of Kurashiki, Japan

[73] Assignee: Mitsubishi Chemical Industries Limited, Tokyo, Japan

[21] Appl. No.: 189,427

[22] Filed: Sep. 22, 1980

[30] Foreign Application Priority Data

Sep. 21, 1979 [JP] Japan .................................. 54-121796

[51] Int. Cl.$^3$ ........................ C07C 45/50; C07C 47/02
[52] U.S. Cl. .................................... 568/454; 568/882; 568/909
[58] Field of Search ........................ 568/454, 909, 882

[56] References Cited

U.S. PATENT DOCUMENTS 4,151,209 4/1979 Paul et al. ............................ 568/454

OTHER PUBLICATIONS

Olivier et al., "Hydrocarbon Processing", Apr. 1970, pp. 112–114.

Cornils et al., "Hydrocarbon Processing", Jun. 1975, pp. 83–91.

*Primary Examiner*—Werren B. Lone
*Attorney, Agent, or Firm*—Sughrue, Mion, Zinn, Macpeak & Seas

[57] ABSTRACT

A process for hydroformylation of olefins is described which comprises a step of reacting olefins with carbon monoxide and hydrogen in the presence of a Group VIII noble metal-triarylphosphine complex catalyst, an excess amount of triarylphosphine, a reaction solvent, and organic high boiling point by-products, taking out the produced aldehyde by separating from the resulted hydroformylation reaction product, and thereafter circulating the residual liquid containing the catalyst and the organic high boiling point by-products to the reaction system as a circulating catalyst liquid, wherein the improvement comprises withdrawing at least a part of said circulating catalyst liquid as an extracted catalyst liquid, distilling off at least a part of the organic high boiling point by-products by steam distillation of said extracted catalyst liquid, and recirculating the bottoms of the steam distillation tower to the hydroformylation reaction step.

12 Claims, No Drawings

PROCESS FOR HYDROFORMYLATION OF OLEFINS

BACKGROUND OF THE INVENTION

1. Field of the Invention

The present invention relates to a process for hydroformylation of olefins.

More particularly, the present invention relates to a process for hydroformylation of olefins using a Group VIII noble metal-triarylphosphine complex as a catalyst which comprises removing organic high boiling point by-products accumulated in the catalyst liquid to maintain the amount of the catalyst liquid within a definite range.

2. Description of the Prior Art

It is a well known fact that Group VIII noble metal-triarylphosphine complex catalysts, particularly rhodium-triarylphosphine complex catalysts, and most especially a rhodium-triphenylphosphine complex catalyst, can be used advantageously as catalysts for the so-called hydroformylation reaction for producing aldehydes having one more carbon atom than the olefin starting material. In recent years, studies concerning these catalysts have been vigorously carried out, because they have excellent catalytic activity and produce straight chain aldehydes in a high yield. These Group VIII noble metal-triarylphosphine complex catalysts, which preferably contain free triarylphosphine, possess the advantage that after the aldehyde produced is separated from the resulting hydroformylation reaction liquid containing the complex catalyst by distillation, stripping with a blowing gas, etc., the residual solution containing the complex catalyst can be recirculated to the hydroformylation step, due to the high thermal stability thereof.

However, reaction by-products having a higher boiling point than the aldehyde produced (referred to herein as "organic high boiling point by-products"), which cannot be separated at the time of the separation of the produced aldehyde by distillation, etc., accumulate in the catalyst liquid when the catalyst liquid is reused with repeated circulation. Generally, the hydroformylation reaction of olefins is carried out industrially while continuously feeding definite amounts of reaction raw materials to a reactor having a certain volume. When these organic high boiling point by-products accumulate in the circulating catalyst liquid, it becomes impossible to maintain the operation in the reactor having a prescribed volume because of increasing of the volume of the catalyst liquid in an amount corresponding to accumulated volume. Even if the amount of the organic high boiling point by-products produced by an individual reaction cycle is very small, the accumulated amount becomes remarkably large due to repetition of the cycle of (1) reaction, (2) separation of the aldehyde produced, and (3) recirculation. Accordingly, it is necessary that not only the aldehyde produced, but also the organic high boiling point by-products, be separated from the reaction system by some means in an amount corresponding to the amount produced.

The following four processes are known for removing the organic high boiling point by-products in order to maintain the amount of the catalyst liquid within a definite range:

(1) a process which comprises purging the catalyst liquid containing said organic high boiling point by-products in a definite amount, corresponding to the amount of organic high-boiling point by-products formed;

(2) a process which comprises introducing a large amount of circulating gas into the catalyst liquid containing the organic high boiling point by-products to carry out gas stripping;

(3) a process which comprises selectively removing the organic high boiling point by-products by an extracting treatment or an adsorption treatment, etc.; and (4) a process which comprises distilling the catalyst liquid containing the organic high boiling point by-products to selectively distill off the organic high boiling point by-products alone.

However, these processes have some problems in the industrial application thereof.

First, according to the process (1), even though the by-products produced can be removed, the Group VIII noble metals and triarylphosphine constituting the catalyst are purged at the same time. Consequently, process (1) is very undesirable from an economic viewpoint.

With respect to process (2), one such known process comprises introducing a large amount of a circulating reaction gas into a reactor which retains all of the high boiling point by-products, the catalyst, and the aldehyde produced, in order to carry out gas-stripping of the aldehyde produced and the high boiling point by-products under the hydroformylation condition (see Japanese Patent Application (OPI) No. 125103/77 (the term "OPI" as used herein refers to a "published unexamined Japanese patent application")). In this process, however, a large amount of circulating gas is required, particularly for the high boiling point by-products having a low vapor pressure. Further, the process requires a very difficult operation wherein the production amount and the removal amount of the high boiling point by-products must be strictly controlled based on the amount of the circulating gas.

According to the process (3), since extraction or adsorption always involves a problem of selectivity, the problem occurs that certain components can be separated while other components cannot be separated. Therefore, it is very difficult to effect industrial practice of this process.

Lastly, according to the process (4), there is a drawback that by-products having a boiling point higher than a certain value cannot be removed, although those having a boiling point up to a certain value can be removed. However, this drawback can be partially overcome by combining with the process (1).

Also, the organic high boiling point by-products form a homogeneous phase in the circulating catalyst liquid together with the Group VIII noble metal-triarylphosphine complex catalyst and the free triarylphosphine. Therefore, in order to effectively circulate the Group VIII noble metal-triarylphosphine complex and the free triarylphosphine to the reaction zone, it is important that not only are the high boiling point by-products selectively separated in the desired amount from the circulating catalyst liquid, but also that the catalytic activity of the circulating catalyst liquid should not be damaged in the separation step.

SUMMARY OF THE INVENTION

An object of the present invention is to provide an industrial process for advantageously practicing the hydroformylation reaction of olefins.

Another object of the present invention is to provide a process for practicing the hydroformylation reaction of olefins while effectively removing the organic high boiling point by-products in the catalyst liquid.

A further object of the present invention is to provide a process for hydroformylation of olefins by which the organic high boiling point by-products can be removed without loss of the activity of the catalyst present in the catalyst liquid.

As a result of extensive studies concerning the process (4) on the basis of the above-described considerations, it has now been found that steam distillation is singularly effective for removing the organic high boiling point by-products from the catalyst liquid containing the Group VIII noble metal-triarylphosphine complex catalyst as the hydroformylation catalyst for olefins, and thus the present invention has been completed on the basis of this knowledge.

Therefore, the present invention provides a process for hydroformylation of olefins which comprises a step of reacting olefins with carbon monoxide and hydrogen in the presence of an excess amount of triarylphosphine, a reaction solvent, and organic high boiling point by-products using Group VIII noble metal-triarylphosphine complex as the catalyst, then separating the aldehyde produced from the resulting hydroformylation reaction product, and thereafter circulating the residual liquid containing the catalyst and the organic high boiling point by-products to the reaction system as a circulating catalyst liquid, wherein the improvement comprises withdrawing at least a part of said circulating catalyst liquid as an extracted catalyst liquid, distilling off at least a part of the organic high boiling point by-products by steam distillation of said extracted catalyst liquid, and recirculating the bottoms of steam distillation tower to the hydroformylation reaction step.

DETAILED DESCRIPTION OF THE INVENTION

The present invention is adopted in case that the organic high boiling point by-products are separated from the catalyst liquid discharged from the reaction system in hydroformylation reaction of olefins using the Group VIII noble metal-triarylphosphine complex catalyst and the residual liquid is reused with circulating to the hydroformylation reaction step.

Olefins that can be used as the raw material for hydroformylation of olefins in the present invention include hydrocarbons having one or more olefinic unsaturated bonds, particularly, straight or branched chain olefins. It is preferred to use straight α-olefins having 2 or more carbon atoms such as ethylene, propylene, 1-butene, 1-hexene, 1-octene, 1-dodecene and 1-tetradecene, etc., but internal olefins such as 2-butene, 2-pentene or 2-hexene, etc., and cyclic olefins may be used, too.

Furthermore, olefins having vinylidene structure such as isobutene can also be used.

A mixed gas composed of carbon monoxide and hydrogen which is also fed to the reactor is generally called water gas or oxo gas, and a typical composition thereof is $H_2/CO$ of from $\frac{1}{3}$ to 20/1 (molar ratio).

The Group VIII nobel metal-triarylphosphine complex catalyst used for hydroformylation reaction is basically provided from the catalyst included in the residual liquid obtained by separating the aldehyde produced from the hydroformylation reaction liquid by distillation and recirculation. However, the catalyst to be fed at initiation of the reaction or for supplementing the supply thereof can be easily prepared using Group VIII noble metal compounds, for example, hydrides, halides, carboxylates, nitrates or sulfates, etc., and triarylphosphine by a known process for preparing complexes. When using this complex catalyst for the reaction, complex previously prepared from the Group VIII noble metal compound and triarylphosphine may be introduced into the reaction system, or the Group VIII noble metal compound and the triarylphosphine may be supplied to the reaction system separately to form the complex catalyst in the reaction system.

Examples of the Group VIII noble metal compounds that can be used for preparing the complexes include ruthenium compounds such as ruthenium trichloride or tetraaminoruthenium hydroxychloride, etc.; rhodium compounds such as rhodium dicarbonyl chloride, rhodium nitrate, rhodium trichloride, rhodium acetate or rhodium sulfate, etc.; palladium compounds such as palladium hydride, palladium chloride, palladium iodide, palladium nitrate, palladium cyanide, palladium acetate or palladium sulfate, etc.; osmium compounds such as osmium trichloride or chloroosmic acid, etc.; iridium compounds such as iridium tribromide, iridium tetrabromide, iridium trifluoride, iridium trichloride or iridium carbonyl, etc.; and platinum compounds such as platinic acid, platinous iodide, sodium hexachloroplatinate, or potassium trichloromonoethyleneplatinate, etc.

As the triarylphosphine ligand, triphenylphosphine is most suitably used. However, it is possible to use various triarylphosphines having substituents which are inactive with respect to the hydroformylation reaction, such as, for example, substituted triphenylphosphines having a lower alkyl group on the phenyl group, such as tri-p-tolylphosphine, tri-m-tolylphosphine, trixylylphosphine or tris(p-ethylphenyl)phosphine, and substituted triphenylphosphines having an alkoxy group on the phenyl group such as tris(p-methoxyphenyl)phosphine, etc. As is known by persons skilled in the art, tertiary phosphines such as triarylphosphine, etc., can be allowed, in general, to coexist in the reaction system in order to improve thermal stability of the complex catalyst and to increase the amount of useful straight chain aldehyde in the aldehydes produced. The amount of such coexistence can be an excess of several ten times to several hundred times (e.g., about 10 to 900) as a molar ratio, based on the moles of the complex catalyst in the reaction system.

The reaction is generally carried out in an inert solvent. As the reaction solvent, those which dissolve raw materials and the catalyst, are inert to the hydroformylation reaction, and have a higher boiling point than the aldehyde produced can be used, by which the resultant reaction liquid can be divided into an aldehyde produced and residual liquid containing the catalyst obtained by the distillation. Examples of them include aromatic hydrocarbons such as benzene, toluene or xylene, etc., saturated aliphatic hydrocarbons such as heptane or decane, etc., esters such as butyl acetate or ethyl butyrate, etc., and alcohols such as butanol, etc. If desired, the aldehyde produced may itself be used as the reaction solvent.

The hydroformylation reaction of olefins in the present invention is usually carried out under atmospheric or higher pressure, preferably at from 30 to 100 kg/cm² oxo gas partial pressure at a reaction temperature of from 50° to 200° C., and preferably from 70° to 150° C., with introducing continuously olefins as the raw materials, the oxo gas and the circulating catalyst liquid into a continuous type reactor.

From the hydroformylation reaction liquid discharged from the reactor, unreacted oxo gas, unreacted olefins, and the aldehyde produced can be separated by known methods, such as gas-liquid separation, evaporation, or distillation, and the catalyst liquid containing the complex catalyst is circulated to the hydroformylation reactor. In this case, at least a part of the circulating catalyst liquid is withdrawn, continuously or intermittently, from the reaction system as an extracted catalyst liquid, in order to avoid accumulation of the by-produced organic high boiling point by-products.

Though the process of the present invention can be applied directly for the extracted catalyst liquid drawn out from the reaction system, it is advantageous to apply the process of the present invention after removing the reaction solvent from the extracted catalyst liquid by a known method, such as distillation, etc. Removal of the reaction solvent from the extracted catalyst liquid is carried out by conventional distillation, for example, normal pressure distillation or vacuum distillation, etc., or by stripping by blowing a gas therethrough. The distillation is preferably carried out so that the solvent content in the extracted catalyst liquid is 20% by weight or less, preferably 5% by weight or less, and most preferably 0%.

The above-described extracted catalyst liquid is subjected to steam distillation directly or after a step for removing solvent. When the extracted catalyst liquid is to be subjected to steam distillation directly, the reaction solvent and the organic high boiling point by-products are distilled off from the top of a steam distillation tower. In this case, if necessary, it is possible to separate the solvent and the organic high boiling point by-products by distillation of the above-described distillate to recover the solvent.

Components in the organic high boiling point by-products are various and complicated, and are chiefly formed by secondary side reactions of aldehydes formed by the hydroformylation reaction. For example, in the hydroformylation reaction of propylene, straight n-butyraldehyde and branched i-butyraldehyde are formed. Since these aldehyde products are vary reactive, they can undergo polymerization or condensation reactions even in the absence of catalyst at a relatively low temperature, to form polycondensation products having a high boiling point. Examples of such polymerization or condensation products having a high boiling point include aldol dimers and trimers produced as self-polymerization products from n-butyraldehyde, 2-ethylhexenal as a condensation dimer thereof, 2-ethylhexanal and 2-ethylhexanol as hydrogenated products thereof, n-butanol as the hydrogenated product of n-butyraldehyde, the dibutylacetal of n-butyraldehyde, etc. Furthermore, i-butyraldehyde also produces dimers and trimers as self-polymerization products thereof by similar reactions to those of n-butyraldehyde, and dimers and trimers, as alternating polymers, from i-butyraldehyde and n-butyraldehyde, and derivatives thereof. It has also been known that organic high boiling point by-products other than the above-described products are produced as by-products during the hydroformylation reaction of propylene. From the above description, it is apparent that the organic high boiling point by-products contain dimers and trimers of the produced aldehydes, which cannot be removed by a mere aldehyde distillation step, because they have a higher boiling point than the aldehydes produced.

In the steam distillation tower, at least a part of the high boiling point by-products in the extracted catalyst liquid is removed together with steam by distillation thereof.

Conditions for operating the steam distillation tower to remove organic high boiling point by-products depend upon the amounts of organic high boiling point by-products to be removed, the physical properties of the organic high boiling point by-products, the amount of the extracted catalyst liquid to be fed to the steam distillation tower, and the concentration of the high boiling point by-products in said extracted catalyst liquid, etc. Accordingly, they cannot be simply prescribed, but they can be controlled by the operation pressure, amount of steam to be fed, external heating, etc., so that the temperature in the bottom of the steam distillation tower is generally maintained at 200° C. or less, preferably at 170° C. or less, and most preferably at 150° C. or less, from the viewpoint of the stability of the catalyst and the prevention of the steam condensing in the tower so as not to mix with the bottoms (discharge liquid from the bottom of a distillation tower) of the tower.

The above-described steam distillation tower can be operated at atmospheric pressure or less. Preferably a reduced pressure is used, and the steam distillation is carried out by a continuous process or a batch process.

In operation of the steam distillation tower, for example, mild operating conditions are used so as to remove only a part of organic high boiling point by-products in the extracted catalyst liquid, when the amount of the organic high boiling point by-products to be removed is much smaller than the amount of organic high boiling point by-products included in the extracted catalyst liquid fed to the steam distillation tower. Severe operating conditions are used so as to remove almost all amounts of the organic high boiling point by-products in the extracted catalyst liquid, when the amount of the organic high boiling point by-products to be removed is nearly equal to the amount of the organic high boiling point by-products in the extracted catalyst liquid fed to the steam distillation tower. Accordingly, the operating condition for the steam distillation tower can be suitably selected on the basis of the relation between the amount of organic high boiling point by-products to be removed and that of the organic high boiling point by-products in the extracted catalyst liquid fed to the steam distillation tower.

Operation of the steam distillation is not restricted, and can be carried out by conventional methods. For example, the operation can be carried out by directly blowing the steam into a distillation container of the steam distillation tower or by heating from the outside while blowing the steam into the distillation container, but it is not limited thereto.

In the steam distillation tower, a desired amount, namely, an amount corresponding to the production amount of organic high boiling point by-products produced as by-products of the reaction, of the organic high boiling point by-products is distilled off from the top of the tower, while the bottoms of the tower containing the organic high boiling point by-products in a reduced amount is discharged from the bottom of the tower. The greater part of the bottoms of the steam distillation tower is circulated to the hydroformylation reaction step, but it is preferred that a part thereof is purged from the system as a waste catalyst liquid in order to remove organic high boiling point by-products which cannot be removed by the steam distillation. Furthermore, when the bottoms of the steam distillation tower discharged from the bottom of the tower comprises two liquid phases (viz., when a part of steam blown condenses to mix therewith), it is preferred to circulate an oil phase to the hydroformylation reaction step after separating the oil and water. After free triarylphosphine is recovered from the waste catalyst liquid purged from the system by a suitable process, such as crystallization, as described in, for example, U.S. patent application Ser. No. 142,686, filed Apr. 22, 1980, the Group VIII noble metal can be recovered by known process, for example, a submerged combustion process, as described in Japanese Patent Application (OPI) No. 39690/75.

A central feature of the present invention is to practice removal of organic high boiling point by-products in the extracted catalyst liquid by a steam distillation process. Thus, in the removal step, steam distillation is required to attain the removal of organic high boiling point by-products without losing the inherent activity of the catalyst contained in the extracted catalyst liquid.

When the removal of organic high boiling point by-products is practiced by a conventional distillation process, for example, a vaccum distillation process, or a gas stripping process comprising blowing a nitrogen gas, etc., the inherent activity of the catalyst remarkably deteriorates in the removal step, if it is attempted to remove the organic high boiling point by-products in an amount corresponding to that by the steam distillation process. Accordingly, the effect of the present invention in removal of the organic high boiling point by-products can be attained by only adopting the steam distillation and cannot be attained by other distillation processes. The reason why the steam distillation is particularly effective for removal of the organic high boiling point by-products is not completely clear, but it is an observed fact that catalytic activity can be maintained only in the case of steam distillation, even if distillation is carried out at the same operating temperature, as shown in the following examples.

As is illustrated in detail in the above, according to the process of the present invention, the organic high boiling point by-products produced in the hydroformylation reaction are removed from the extracted catalyst liquid essentially without damaging any catalytic activity, and the bottoms of the steam distillation tower can be reused by recirculating them to the hydroformylation reaction step. Accordingly, the industrial value of the present invention is significant.

Further, the hydroformylation reaction of olefins can be practiced industrially and more advantageously, when the organic high boiling point by-products which cannot be removed by even steam distillation are removed by purging a part of the bottoms of the steam distillation tower from the reaction system as the waste catalyst liquid, and the Group VIII noble metal and triarylphosphine are separated and recovered from the waste catalyst liquid by a suitable process, because useful expensive triarylphosphine and Group VIII noble metal can be recovered in a high yield and high purity from the waste catalyst liquid of the hydroformylation reaction and can be reused for the hydroformylation reaction system. Moreover, according to this process, it is possible to remarkably reduce the waste catalyst liquid to be purged from the system in order to recover the Group VIII noble metal and the triarylphosphine. Accordingly, the industrial value of the present invention is significant in this respect also.

In the following, the present invention is illustrated in greater detail with reference to examples, but the present invention is not limited to the examples so far as it does not depart from the gist thereof.

EXAMPLE 1

Removal of organic high boiling point by-products from extracted catalyst liquid:

In a presence of an excess amount of triphenylphosphine, propylene was subjected to hydroformylation reaction using a rhodium-triphenylphosphine complex catalyst in a continuous flow reactor. After unreacted olefin and the aldehyde produced were separated from the resulting hydroformylation reaction liquid, a part of a catalyst liquid for circulating to the hydroformylation reaction system was drawn out as the extracted catalyst liquid. A major part of the toluene solvent was separated from the above-described extracted catalyst liquid by conventional distillation to obtain a residual liquid having the composition shown in Table 1 (referred to herein as Extracted Catalyst Liquid (I)). This Extracted Catalyst Liquid (I) was placed in a 500 ml pear-shaped flask kettle equipped with a steam blowing inlet, a condenser and a distillate receiver. While keeping the temperature of the kettle at 150° C., steam heated to 1,000 mm of column of water was fed into the flask kettle at a rate of 200 N l/hr to carry out steam distillation at normal atmospheric pressure. As a result, 75.3 g of oil phase distillate was obtained. From analysis of the resulting oil phase, it was found that the distillation amount of the organic high boiling point by-products was 62 g and the major part of the other oil phase distillate was toluene. The removal ratio of organic high boiling point by-products was 88% (=62/70×100). Further, 100% of rhodium and 99% of triphenylphosphine remained in the kettle, which were drawn out as the bottoms.

TABLE 1

| Composition of Extracted Catalyst Liquid (I) | |
| --- | --- |
| Component | Weight (%) |
| Toluene | 12.3 |
| Organic high boiling point by-products*1 | 70.0 |
| Triphenylphosphine | 15.7 |
| Triphenylphosphine oxide | 0.4 |
| The other by-products having low boiling point | 1.6 |
| Total | 100 |
| Rhodium*2 | 156 mg/l |

*1By-products having a higher boiling point than toluene
*2Value calculated as metal, which is excepted from calculation of % by weight due to its presence in a very small amount.

EXAMPLE 2

Experiment for measuring the activity of the catalyst in extracted catalyst liquid before steam distillation and the catalyst in the bottoms remaining in the kettle after steam distillation:

(a) Experiment 1

50 ml of Extracted Catalyst Liquid (I) in Example 1 was placed in an autoclave having 200 ml of the volume equipped with an electromagnetic up-down stirrer. 10.5 g of propylene was added thereto by distillation. After the temperature of the autoclave was raised to 110° C., an oxo gas of $H_2/CO=4.0/1$ (molar ratio) was introduced at a pressure of 50 kg/cm$^2$G, and then an oxo gas of $H_2/CO=1.0/1$ (molar ratio) was fed to the autoclave from a high pressure gas holder through a pressure controller. The rate constant (first-order reaction) measured from the consumption rate of oxo gas in the high pressure gas holder was 2.8 hr$^{-1}$.

(b) Experiment 2

The reaction was carried out in the same manner as Experiment 1, except for using a catalyst liquid having the same concentration as Extracted Catalyst Liquid (I) which was prepared by adding toluene and high boiling point by-products distilled by steam distillation to the bottoms of the kettle obtained in Example 1. The rate constant (first-order reaction) measured was 3.0 hr$^{-1}$. Accordingly, the relative activity of catalyst (=rate constant after distillation operation/rate constant before distillation operation) is 1.07 (=3.0/2.8).

EXAMPLE 3

Removal of organic high boiling point by-products from extracted catalyst liquid:

Steam distillation was carried out in the same manner as in Example 1, except that the temperature of the kettle of steam distillation was 120° C. and the pressure was 50 mmHg to remove organic high boiling point by-products from the Extracted Catalyst Liquid (I). Analysis of the distillate showed that the removal ratio of organic high boiling point by-products was 87%.

When catalytic activity was measured by the same manner as in Example 2, the rate constant (first-order reaction) after distillation operation was 2.9 hr$^{-1}$ and the relative activity was 1.02.

COMPARATIVE EXAMPLES 1 & 2

Removal of organic high boiling point by-products from extracted catalyst liquid by distillation treatment other than steam distillation:

Removal of organic high boiling point by-products from Extracted Catalyst Liquid (I) was carried out in the same manner as in Example 1, except that distillation was carried out by the distillation technique and at a pressure as shown in Table 2. The removal ratio of organic high boiling point by-products, the rate constant (first-order reaction) after distillation (measured in the same manner as in Example 2), and the relative activity are shown in Table 2.

TABLE 2

| | Comparative Example 1 | Comparative Example 2 |
|---|---|---|
| Distillation form | Distillation with blowing nitrogen | Vacuum distillation |
| Pressure (mm Hg) | 760 | 2 |
| Removal ratio (%) | 88 | 84 |
| Rate constant (first-order reaction) after distillation (hr$^{-1}$) | 2.2 | 2.3 |
| Relative activity | 0.78 | 0.82 |

As is clear from the results of Examples and Comparative Examples, under conditions of obtaining nearly the same removal ratio of organic high boiling point by-products, removal of organic high boiling point by-products can be carried out without causing deterioration of activity of the catalyst according to the steam distillation process of the present invention, while the activity of the catalyst is greatly reduced by vacuum distillation or gas stripping with nitrogen.

While the invention has been described in detail and with reference to specific embodiments thereof, it will be apparent to one skilled in the art that various changes and modifications can be made therein without departing from the spirit and scope thereof.

What is claimed is:

1. A process for hydroformylation of olefins which comprises a step of reacting aliphatic mono-olefins with carbon monoxide and hydrogen using a Group VIII noble metal-triarylphosphine complex catalyst in the presence of an excess amount of triarylphosphine, a reaction solvent, and organic high boiling point by-products, then separating the aliphatic saturated aldehyde produced from the resulting hydroformylation reaction product, and thereafter circulating the residual liquid containing the catalyst and the organic high boiling point by-products to the reaction system as a circulating catalyst liquid, wherein the improvement comprises withdrawing at least a part of said circulating catalyst liquid as an extracted catalyst liquid, distilling off at least a part of the organic high boiling point by-products by steam distillation of said extracted catalyst liquid, and recirculating the bottoms of the steam distillation tower to the hydroformylation reaction step.

2. A process according to claim 1 wherein the Group VIII noble metal is rhodium.

3. A process according to claim 1 or 2 wherein the triarylphosphine is triphenylphosphine.

4. A process according to claim 1 or 2 wherein the steam distillation of said extracted catalyst liquid is carried out after a part or the whole of the reaction solvent is removed from the extracted catalyst liquid.

5. A process according to claim 3 wherein the steam distillation of said extracted catalyst liquid is carried out after a part or the whole of the reaction solvent is removed from the extracted catalyst liquid.

6. A process according to claim 1 wherein the ratio of hydrogen carbon monoxide is from ⅓ to 20/1.

7. A process according to claim 1 wherein the olefin is an α-olefin having 2 or more carbon atoms.

8. A process according to claim 1 wherein the reaction is carried out at atmospheric or higher pressure of oxo gas and at a reaction temperature of from 50° to 200° C.

9. A process according to claim 8 wherein the oxo gas pressure is from 30 to 100 kg/cm$^2$ and the temperature is from 70° to 150° C.

10. A process according to claim 1, wherein the steam distillation is conducted at atmospheric pressure or lower.

11. A process according to claim 10, wherein catalyst activity is not reduced during the steam distillation.

12. A process according to claim 11, wherein catalyst activity is increased during the steam distillation.

* * * * *